(12) United States Patent
Jiang et al.

(10) Patent No.: US 12,296,199 B2
(45) Date of Patent: *May 13, 2025

(54) NEUTRON CAPTURE THERAPY SYSTEM (71) Applicant: Neuboron Therapy System Ltd., Fujian (CN)

(72) Inventors: Tao Jiang, Fujian (CN); Wei-Lin Chen, Fujian (CN)

(73) Assignee: NEUBORON THERAPY SYSTEM LTD., Fujian (CN)

( * ) Notice: Subject to any disclaimer, the term of this patent is extended or adjusted under 35 U.S.C. 154(b) by 1308 days.

This patent is subject to a terminal disclaimer.

(21) Appl. No.: 17/145,562

(22) Filed: Jan. 11, 2021

(65) Prior Publication Data

US 2021/0146163 A1 May 20, 2021

Related U.S. Application Data (63) Continuation of application No. PCT/CN2019/087928, filed on May 22, 2019.

(30) Foreign Application Priority Data

Aug. 31, 2018 (CN) .......................... 201811011377.1
Aug. 31, 2018 (CN) .......................... 201811014166.3

(51) Int. Cl.
*A61N 5/10* (2006.01)
*E04B 1/92* (2006.01)
(Continued)

(52) U.S. Cl.
CPC .......... *A61N 5/1077* (2013.01); *E04C 5/0604* (2013.01); *E04C 5/07* (2013.01);
(Continued)

(58) Field of Classification Search
CPC ............ A61N 5/1078; A61N 2005/109; A61N 2005/1094; A61N 5/1077; A61N 5/103;
(Continued)

(56) References Cited

U.S. PATENT DOCUMENTS 3,211,623 A * 10/1965 Tower ...................... G21C 1/20
976/DIG. 134
4,705,661 A * 11/1987 Cransac ................. G21C 13/00
376/268
(Continued)

FOREIGN PATENT DOCUMENTS

CN 101529530 A 9/2009
CN 102260812 A 11/2011
(Continued)

OTHER PUBLICATIONS

European Patent Office, PCT/CN2019/087928, Sep. 24, 2021, Germany.
International Search Report of PCT/CN2019/087928, Jul. 23, 2019.

*Primary Examiner* — David A Vanore
(74) *Attorney, Agent, or Firm* — Troutman Pepper Locke LLP; Tim Tingkang Xia, Esq.

(57) ABSTRACT

A neutron capture therapy system includes a neutron generating device and a beam shaping assembly. The neutron capture therapy system further includes a concrete wall accommodating the neutron generating device and the beam shaping assembly and shielding radiations generated by the neutron generating device and the beam shaping assembly, the concrete wall and a reinforcing portion at least partially disposed in the concrete wall are provided to support the beam shaping assembly, and more than 90% of weight of a material of the reinforcing portion is composed of at least one element of C, H, O, N, Si, Al, Mg, Li, B, Mn, Cu, Zn, S, Ca, and Ti. In the neutron capture therapy system, the reinforcing portion disposed in the concrete wall has good
(Continued)

anti-activation performance. Therefore, compared with a conventional reinforced concrete structure, the radiation is further attenuated.

19 Claims, 7 Drawing Sheets

(51) Int. Cl.
  *E04C 5/06* (2006.01)
  *E04C 5/07* (2006.01)
  *G21F 1/04* (2006.01)
  *H05H 6/00* (2006.01)
(52) U.S. Cl.
  CPC ........ *G21F 1/042* (2013.01); *A61N 2005/109* (2013.01); *A61N 2005/1094* (2013.01); *E04B 2001/925* (2013.01); *H05H 2006/007* (2013.01)
(58) Field of Classification Search
  CPC .......... A61N 5/1042; G21G 4/02; G21K 5/04; G21K 5/02; H05H 3/06; G21F 1/042; G21F 3/00
  See application file for complete search history.

(56) References Cited

U.S. PATENT DOCUMENTS

| | | | | |
|---|---|---|---|---|
| 5,583,900 A * | 12/1996 | Kasahara | ................ | C22C 38/58 376/288 |
| 9,486,646 B2 | 11/2016 | Paliwal et al. | | |
| 11,826,583 B2 * | 11/2023 | Jiang | ........................ | G21G 4/02 |
| 2004/0254419 A1 * | 12/2004 | Wang | ...................... | A61L 31/18 424/1.11 |
| 2005/0025797 A1 * | 2/2005 | Wang | ..................... | B82Y 25/00 424/422 |
| 2009/0064604 A1 * | 3/2009 | Yamaguchi | ........... | E02D 29/045 52/169.6 |
| 2010/0296618 A1 * | 11/2010 | Sejvar | ...................... | G21F 3/00 376/293 |
| 2011/0198516 A1 | 8/2011 | Fan et al. | | |
| 2012/0261597 A1 * | 10/2012 | Graves | ...................... | G21F 1/00 29/592 |
| 2013/0139727 A1 * | 6/2013 | Constantz | ........... | C04B 16/0641 106/656 |
| 2014/0260034 A1 * | 9/2014 | Ciuperca | ................... | E04C 2/26 52/405.3 |
| 2014/0364677 A1 * | 12/2014 | Katayose | ................. | G21K 1/10 600/1 |
| 2017/0073270 A1 * | 3/2017 | Shao | ........................ | E04C 1/00 |
| 2017/0367897 A1 * | 12/2017 | Estrada, Jr. | ......... | A61F 5/05866 |
| 2018/0025799 A1 * | 1/2018 | Kim | ........................ | G21F 1/12 250/515.1 |
| 2018/0071949 A1 * | 3/2018 | Giles | ...................... | B28B 1/001 |
| 2018/0111876 A1 * | 4/2018 | Zampini | ............. | C04B 16/0625 |
| 2018/0258659 A1 * | 9/2018 | LeBlanc | ................... | E04B 7/20 |

FOREIGN PATENT DOCUMENTS

| | | |
|---|---|---|
| CN | 102695544 A | 9/2012 |
| CN | 106211727 A | 12/2016 |
| CN | 106351474 A | 1/2017 |
| CN | 106474635 A | 3/2017 |
| CN | 206835439 U | 1/2018 |
| EP | 2921206 A1 | 9/2015 |
| EP | 3136400 A1 | 3/2017 |
| JP | H01147399 A | 6/1989 |
| JP | 01147399 | 9/1989 |
| JP | 2000514552 A | 10/2000 |
| JP | 2017176357 A | 10/2017 |
| JP | 2021528213 A | 10/2021 |
| WO | 9800258 A1 | 1/1998 |
| WO | 2018113274 A1 | 6/2018 |

* cited by examiner

NEUTRON CAPTURE THERAPY SYSTEM

CROSS-REFERENCE TO RELATED PATENT APPLICATION

This application is a continuation application of International Application No. PCT/CN2019/087928, filed on May 22, 2019, which claims priority to Chinese Patent Application No. 201811011377.1, filed on Aug. 31, 2018; Chinese Patent Application No. 201811014166.3, filed on Aug. 31, 2018, the disclosures of which are hereby incorporated by reference.

FIELD

The present disclosure relates to a radiation irradiation system, and in particular to a neutron capture therapy system.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

As atomics moves ahead, such radiotherapy as Cobalt-60, linear accelerators and electron beams has been one of major means to cancer therapy. However, conventional photon or electron therapy has been undergone physical restrictions of radioactive rays; for example, many normal tissues on a beam path will be damaged as tumor cells are destroyed. On the other hand, sensitivity of tumor cells to the radioactive rays differs greatly, so in most cases, conventional radiotherapy falls short of treatment effectiveness on radioresistant malignant tumors (such as glioblastoma multiforme and melanoma).

For the purpose of reducing radiation damage to the normal tissue surrounding a tumor site, target therapy in chemotherapy has been employed in the radiotherapy. While for high-radioresistant tumor cells, radiation sources with high RBE (relative biological effectiveness) including such as proton, heavy particle and neutron capture therapy have also developed. Among them, the neutron capture therapy combines the target therapy with the RBE, such as the boron neutron capture therapy (BNCT). By virtue of specific grouping of boronated pharmaceuticals in the tumor cells and precise neutron beam regulation, BNCT is provided as a better cancer therapy choice than conventional radiotherapy.

Various radiations are generated during radiotherapy. For example, neutrons and photons of low-energy to high-energy are generated during boron neutron capture therapy. These radiations may cause different degrees of damage to normal human tissues. Therefore, in the field of radiotherapy, how to reduce radiation pollution to the external environment, medical staff or normal tissues of irradiated subjects is an extremely important issue while effective treatment is achieved. A radiotherapy device is usually placed in a building constructed by concrete to isolate the radiation that may be generated by the device. In a general reinforced concrete structure, rebars are activated by neutrons to generate radioactive isotopes with a relatively long half-life. For example, the half-life of Cobalt-60 is 5.27 years, forming radioactive waste with a long decaying time, leading to negative impact on environment and radiation safety.

Therefore, it is necessary to propose a new technical solution to resolve the foregoing problem.

SUMMARY

To resolve the foregoing problem, an aspect of the present disclosure provides a neutron capture therapy system, including a neutron generating device and a beam shaping assembly. The neutron generating device includes an accelerator and a target, and a charged particle beam generated by acceleration of the accelerator acts with the target to generate a neutron beam. The beam shaping assembly includes a reflector, a moderator, a thermal neutron absorber, a radiation shield, and a beam exit. The moderator is configured to moderate the neutrons generated from the target to an epithermal neutron energy range, the reflector surrounds the moderator and directs deviating neutrons back to the moderator to enhance intensity of an epithermal neutron beam, the thermal neutron absorber is provided to absorb thermal neutrons to avoid overdosing in superficial normal tissues during treatment, and the radiation shield around the beam exit is disposed at the rear of the reflector for shielding leaking neutrons and photons so as to reduce dose to normal tissues in a non-irradiation area. The neutron capture therapy system further includes a concrete wall accommodating the neutron generating device and the beam shaping assembly, the concrete wall and a reinforcing portion at least partially disposed in the concrete wall are provided to support the beam shaping assembly, and more than 90% of weight of the material of the reinforcing portion is composed of at least one element of C, H, O, N, Si, Al, Mg, Li, B, Mn, Cu, Zn, S, Ca, and Ti. The concrete structure may shield leaking neutrons and other radiations in a working process of the neutron capture therapy system. The reinforcing portion may increase the rigidity, tensile strength, and bearing capacity of the concrete. The material of the reinforcing portion is composed of elements having a cross section hardly acting with neutrons or generating radioactive isotopes with a short half-life after being activated by neutrons. Because the radioactivity derived from neutron activation is relatively low, a secondary radiation dose is appropriately suppressed, and future device dismantlement is facilitated.

Implementations of this aspect may include one or more of the following features.

Further, elastic modulus of the material of the reinforcing portion is not less than 40 GPa, yield strength of the material is not less than 100 MPa, and ultimate strength of the material is not less than 200 MPa.

Further, half-life of radioactive isotopes generated after the reinforcing portion is activated by neutrons is less than 1 year.

Further, the material of the reinforcing portion is at least partially an aluminum alloy, a carbon fiber composite material or a glass fiber composite material. The half-life of aluminum activated by neutrons is relatively short, and the carbon fiber composite material or the glass fiber composite material has good anti-activation performance. Therefore, compared with a conventional reinforced concrete structure, the radioactivity derived from neutron activation is greatly reduced within a limited time. Further, the aluminum alloy is an aluminum-magnesium alloy, the carbon fiber composite material is a carbon fiber-resin composite material, the glass fiber composite material is a glass fiber-resin composite material. The aluminum-magnesium alloy, carbon fiber composite material or glass fiber composite material has relatively excellent mechanical properties.

Further, the neutron capture therapy system further includes a treatment table and a collimator, the collimator is disposed at the rear of the beam exit to converge the neutron beam, the neutron beam generated by the neutron generating device passes through the beam shaping assembly and the collimator to irradiate an irradiated subject on the treatment table, and a radiation shielding device is disposed between the irradiated subject and the beam exit to shield normal tissues of the irradiated subject from irradiation by beams from the beam exit. There may be one or more targets. The charged particle beam may selectively act with one or several targets or may simultaneously act with a plurality of targets, to generate one or more therapeutic neutron beams. Corresponding to the quantity of the targets, there may also be one or more beam shaping assemblies, collimators, and treatment tables.

Further, the neutron capture therapy system further includes a charged particle beam generation room and an irradiation room, the irradiated subject on the treatment table receives treatment of neutron beam irradiation in the irradiation room, the charged particle beam generation room accommodates the accelerator, and the concrete wall includes a partition wall between the charged particle beam generation room and the irradiation room. The partition wall may completely separate the irradiation room from the charged particle beam generation room. Alternatively, the partition wall may partially separate the irradiation room from the charged particle beam generation room, and the irradiation room is in communication with the charged particle beam generation room. A plurality of treatment tables may be disposed in the same irradiation room, or an individual irradiation room may be disposed for each treatment table.

More particularly, the beam shaping assembly is disposed in the partition wall and supported by the partition wall, an accommodating cavity is provided in the partition wall, the beam shaping assembly is mounted in the accommodating cavity, and the accommodating cavity penetrates the partition wall in the thickness direction.

More particularly, the neutron generating device further includes a beam transmitter, the beam transmitter transmits the charged particle beam generated by the accelerator to the target, a through hole is provided in the partition wall, the beam transmitter passes through the through hole, the reinforcing portion is at least partially disposed in the partition wall, and the beam shaping assembly is supported on the reinforcing portion.

Another aspect of the present disclosure provides a neutron capture therapy system including a neutron generating device, a beam shaping assembly, and a support device for holding the beam shaping assembly. the neutron generating device is configured to generate a neutron beam; the beam shaping assembly is configured to adjust beam quality of the neutron beam; the support device includes an accommodating cavity, the beam shaping assembly is mounted in the accommodating cavity, and the support device further includes a concrete wall and a reinforcing portion at least partially disposed in the concrete wall. The concrete structure may shield leaking neutrons and other radiations in a working process. The beam shaping assembly is very sensitive to deformation and requires that the support structure have sufficient stiffness. The reinforcing portion disposed in the concrete may increase the rigidity, tensile strength, and bearing capacity of the concrete.

Implementations of this aspect may include one or more of the following features.

Further, elastic modulus of a material of the reinforcing portion is not less than 40 GPa, yield strength of the material is not less than 100 MPa, and ultimate strength of the material is not less than 200 MPa.

Further, more than 90% of weight of a material of the reinforcing portion is composed of at least one element of C, H, O, N, Si, Al, Mg, Li, B, Mn, Cu, Zn, S, Ca, and Ti. The material of the reinforcing portion is composed of elements having a cross section hardly acting with neutrons or generating radioactive isotopes with a short half-life after being activated by neutrons. Because the radioactivity derived from neutron activation is relatively low, a secondary radiation dose is appropriately suppressed, and future device dismantlement is facilitated.

Further, half-life of radioactive isotopes generated after the reinforcing portion is activated by neutrons is less than 1 year.

Further, the accommodating cavity is a through hole formed in the concrete wall, the reinforcing portion includes a circular ring, a frame, and distribution ribs; the circular ring is disposed around the beam shaping assembly, the frame is disposed around the circular ring, the distribution ribs are distributed in the concrete at a preset spacing in the horizontal direction, the vertical direction, and the thickness direction of the concrete, the distribution ribs at least partially pass through the frame or are at least partially propped on the frame, the distribution ribs are at least partially propped on the circular ring. The circular ring and the frame increase the rigidity and tensile strength of the concrete. The distribution ribs may prevent concrete from cracking and improve the overall performance of the wall body.

More particularly, materials of the circular ring and the frame are an aluminum alloy, a carbon fiber composite material or a glass fiber composite material; and a material of the distribution ribs is steel, an aluminum alloy, a carbon fiber composite material or a glass fiber composite material. The half-life of aluminum activated by neutrons is relatively short, and the carbon fiber composite material or the glass fiber composite material has good anti-activation performance. Therefore, compared with a conventional reinforced concrete structure, the radioactivity derived from neutron activation is greatly reduced within a limited time. Further, the aluminum alloy is an aluminum-magnesium alloy, the carbon fiber composite material is a carbon fiber-resin composite material, the glass fiber composite material is a glass fiber-resin composite material. The aluminum-magnesium alloy, carbon fiber composite material or glass fiber composite material has relatively excellent mechanical properties.

More particularly, the circular ring is a section bar or constructed by a rib, and the frame is section bars or constructed by ribs. When the frame is section bars, the frame includes horizontal frame-section beams and vertical frame-section pillars, and the horizontal frame-section beams and the vertical frame-section pillars are connected by screw bolts or welding. The concrete has high compressive strength but low tensile strength, and the strain slowly increases with time under a constant stress. The aluminum-magnesium alloy section bars have adequate tensile strength and shear strength and high stiffness, and the strain does not increase with time under a constant stress. The carbon fiber-resin composite material or glass fiber-resin composite material has high tensile strength, and may compensate for insufficient mechanical properties and material characteristics of the concrete. When the frame is constructed by ribs, the frame includes horizontal skeletons and vertical skeletons. The horizontal skeletons include horizontal longitudinal ribs and stirrups, and the vertical skeletons include vertical longitudinal ribs and stirrups. The concrete has adequate compressive capacity and bearing capacity. The aluminum-magnesium alloy ribs have adequate tensile capacity and bearing capacity, and the aluminum-magnesium alloy ribs arranged at a tension-bearing position may compensate for insufficient tensile strength of the concrete. The carbon fiber-resin composite material or glass fiber-resin composite material has high tensile strength. The stirrups may be arranged to improve the shear performance of the wall body.

Further, the reinforcing portion includes a first reinforcing portion and a second reinforcing portion, the first reinforcing portion is disposed in the concrete wall, and the second reinforcing portion at least partially extends from the concrete wall.

More particularly, the first reinforcing portion includes a circular ring, a frame, and distribution ribs. The circular ring and the frame increase the rigidity and tensile strength of the concrete. The distribution ribs may prevent concrete from cracking and improve the overall performance of the wall body.

, the circular ring is a section bar or constructed by a rib, the frame is constructed by horizontal frame-section beams or horizontal skeletons, and the horizontal skeletons include horizontal longitudinal ribs and stirrups.

More particularly, the second reinforcing portion includes a horizontal support plate and side plates connecting the support plate to the first reinforcing portion. Further, a flange is disposed on a side, facing the first reinforcing portion, of the support plate, the flange forms the accommodating cavity and limits the beam shaping assembly in the horizontal direction, a through hole is formed in the support plate, and the neutron beam emerges from the through hole after passing through the beam shaping assembly.

More particularly, a material of the second reinforcing portion is steel, an aluminum alloy, a carbon fiber composite material, or a glass fiber composite material. The half-life of aluminum activated by neutrons is relatively short, and the carbon fiber composite material or the glass fiber composite material has good anti-activation performance. Therefore, compared with a conventional reinforced concrete structure, the radioactivity derived from neutron activation is greatly reduced within a limited time. Further, the aluminum alloy is an aluminum-magnesium alloy, the carbon fiber composite material is a carbon fiber-resin composite material, and the glass fiber composite material is a glass fiber-resin composite material. The aluminum-magnesium alloy, carbon fiber composite material or glass fiber composite material has relatively excellent mechanical properties.

A third aspect of the present disclosure provides a building for a neutron irradiation system, where the building is a concrete structure accommodating the neutron irradiation system, a reinforcing portion is disposed in the concrete structure, and more than 90% of weight of a material of the reinforcing portion is composed of at least one element of C, H, O, N, Si, Al, Mg, Li, B, Mn, Cu, Zn, S, Ca, and Ti. The concrete structure may shield leaking neutrons and other radiations in a working process of the neutron irradiation system. The reinforcing portion may increase the rigidity, tensile strength, and bearing capacity of the concrete. The material of the reinforcing portion is composed of elements having a cross section hardly acting with neutrons or generating radioactive isotopes with a short half-life after being activated by neutrons. Because the radioactivity derived from neutron activation is relatively low, a secondary radiation dose is appropriately suppressed, and future device dismantlement is facilitated.

Implementations of this aspect may include one or more of the following features.

Further, the reinforcing portion includes horizontal and/or vertical distribution ribs, the horizontal and/or vertical distribution ribs are distributed in the concrete structure at a preset spacing in the horizontal direction, the vertical direction, and the thickness direction of the concrete, and the distribution ribs may prevent concrete from cracking and improve the overall performance of the wall body.

Further, elastic modulus of the material of the reinforcing portion is not less than 40 GPa, yield strength of the material is not less than 100 MPa, and ultimate strength of the material is not less than 200 MPa.

Further, half-life of radioactive isotopes generated after the reinforcing portion is activated by neutrons is less than 1 year.

Further, the material of the reinforcing portion is at least partially an aluminum alloy, a carbon fiber composite material or a glass fiber composite material. The half-life of aluminum activated by neutrons is relatively short, and the carbon fiber composite material or the glass fiber composite material has good anti-activation performance. Therefore, compared with a conventional reinforced concrete structure, the radioactivity derived from neutron activation is greatly reduced within a limited time.

Further, the aluminum alloy is an aluminum-magnesium alloy, the carbon fiber composite material is a carbon fiber-resin composite material, the glass fiber composite material is a glass fiber-resin composite material, and the concrete of the concrete structure is boron-containing barite concrete. The aluminum-magnesium alloy, carbon fiber composite material or glass fiber composite material has relatively excellent mechanical properties. The boron-containing concrete has better neutron absorption property, so that the radiation shielding effect of the concrete is enhanced, and metal materials in the concrete may also be exposed to a smaller amount of neutrons.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment.

DETAILED DESCRIPTION OF THE DISCLOSURE

Embodiments of the present invention are further described below in detail with reference to the accompanying drawings, to enable a person skilled in the art to implement the present invention with reference to the text of the specification.

Figure 1:
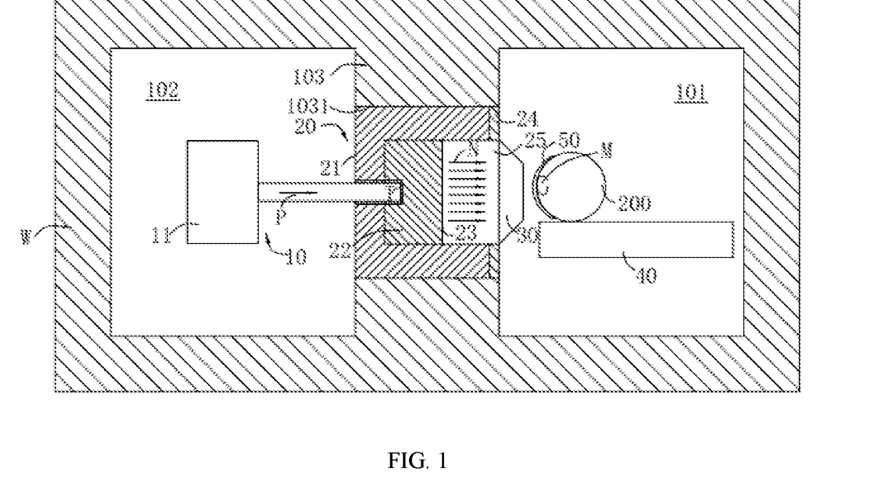
FIG. 1 is a schematic structural diagram of a neutron capture therapy system according to an embodiment of the present disclosure.
Figure 2:
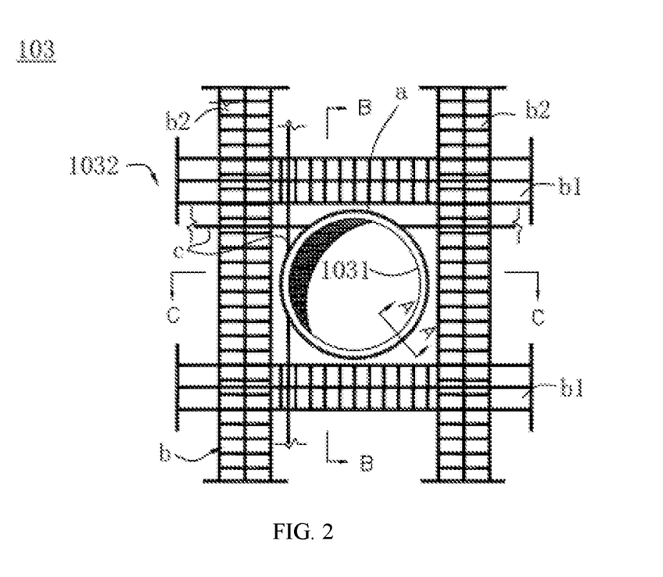
FIG. 2 is a schematic diagram of a support structure of a beam shaping assembly of a neutron capture therapy system according to a first embodiment of the present disclosure.
Figure 3:
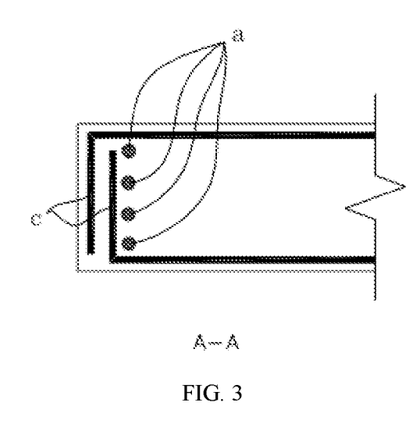
FIG. 3 is a schematic sectional view along A-A in FIG. 2.
Figure 4:
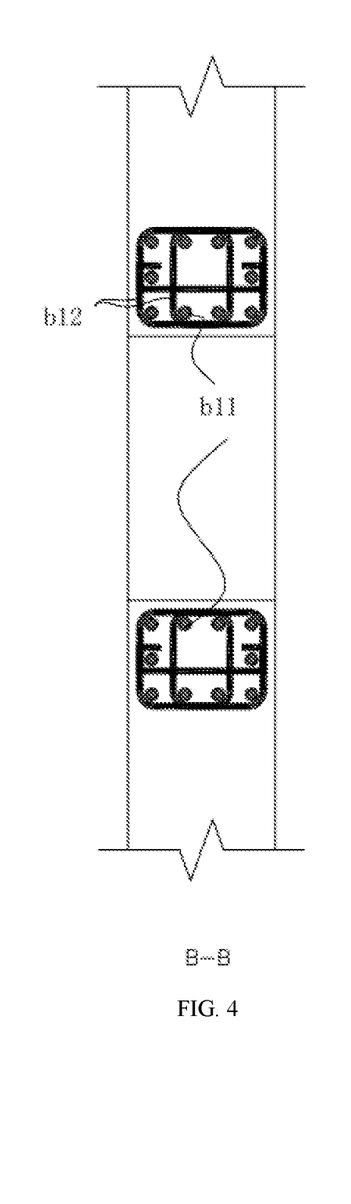
FIG. 4 is a schematic sectional view along B-B in FIG. 2.
Figure 5:
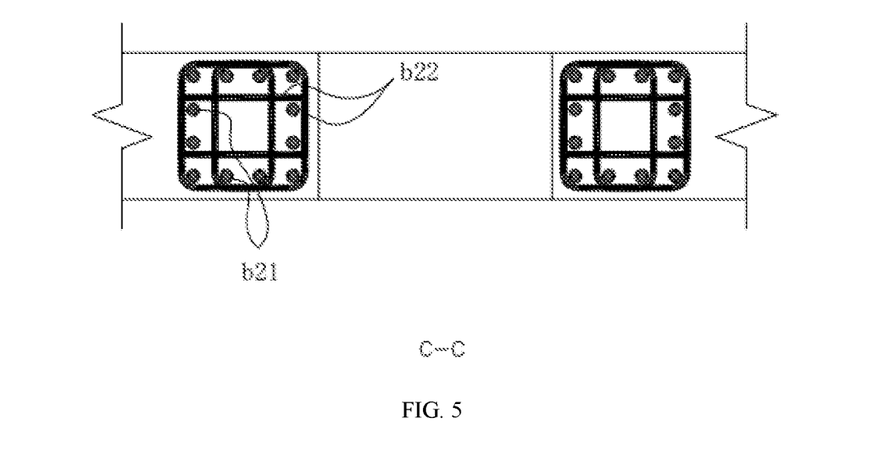
FIG. 5 is a schematic sectional view along C-C in FIG. 2.
Figure 6:
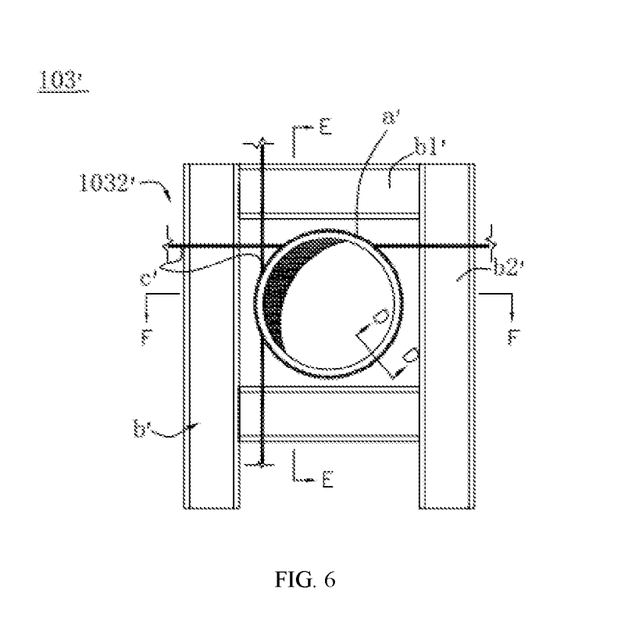
FIG. 6 is a schematic diagram of a support structure of a beam shaping assembly of a neutron capture therapy system according to a second embodiment of the present disclosure.
Figure 7:
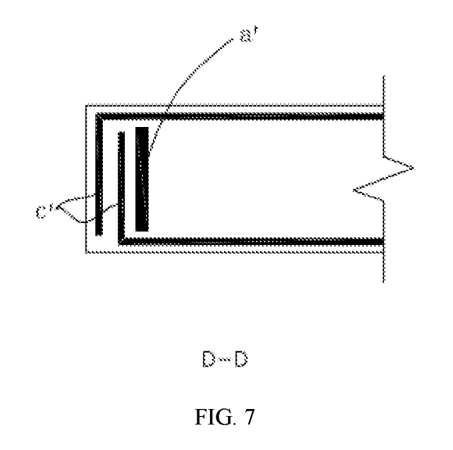
FIG. 7 is a schematic sectional view along D-D in FIG. 6.
Figure 8:
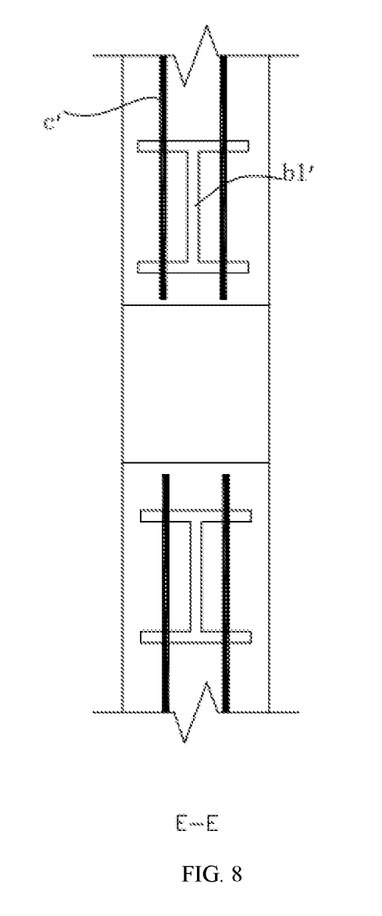
FIG. 8 is a schematic sectional view along E-E in FIG. 6.
Figure 9:
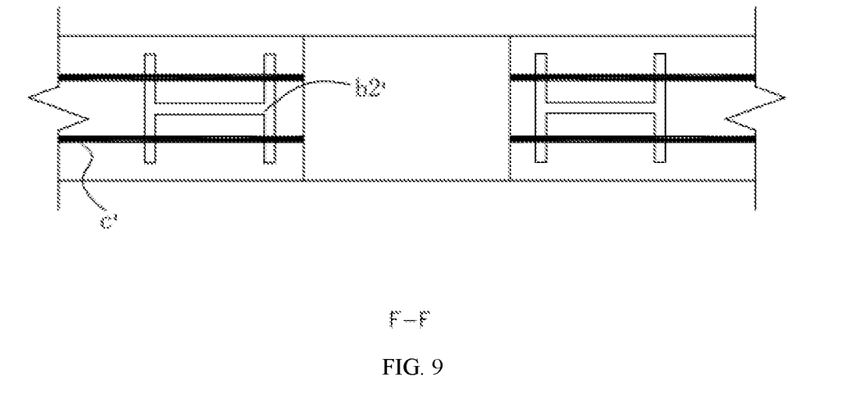
FIG. 9 is a schematic sectional view along F-F in FIG. 6.

As shown in FIG. 1, a neutron capture therapy system in this embodiment is preferably a boron neutron capture therapy system 100, which includes a neutron generating device 10, a beam shaping assembly 20, a collimator 30, and a treatment table 40. The neutron generating device 10 includes an accelerator 11 and a target T, and the accelerator 11 accelerates charged particles (such as protons, deuterons, etc.) to generate a charged particle beam P such as a proton beam, and the charged particle beam P irradiates the target T and acts with the target T to generate a neutron beam N, and the target T is a metal target. Suitable nuclear reactions are always determined according to such characteristics as desired neutron yield and energy, available accelerated charged particle energy and current and materialization of the metal target, among which the most discussed two are $^7$Li (p, n) $^7$Be and $^9$Be (p, n) $^9$B and both are endothermic reaction. Their energy thresholds are 1.881 MeV and 2.055 MeV respectively. Epithermal neutrons at a keV energy level are considered ideal neutron sources for BNCT. Theoretically, bombardment with lithium target using protons with energy slightly higher than the thresholds may produce neutrons relatively low in energy, so the neutrons may be used clinically without many moderations. However, Li (lithium) and Be (beryllium) and protons of threshold energy exhibit not high action cross section. In order to produce sufficient neutron fluxes, high-energy protons are usually selected to trigger the nuclear reactions. The target, considered perfect, is supposed to have the advantages of high neutron yield, a produced neutron energy distribution near the epithermal neutron energy range (see details thereinafter), little strong-penetration radiation, safety, low cost, easy accessibility, high temperature resistance etc. But in reality, no nuclear reactions may satisfy all requests. The target in these embodiments of the present disclosure is made of lithium. However, well known by those skilled in the art, the target materials may be made of other metals besides lithium or beryllium, for example, tantalum (Ta) or tungsten (W). The target T may be in the shape of a disk, or may be in other solid shapes, or a liquid (liquid metal) may be used. The accelerator 11 may be a linear accelerator, a cyclotron, a synchrotron, a synchrocyclotron, and the neutron generating device 10 may further be a nuclear reactor without using an accelerator and a target. No matter BNCT neutron sources are from the nuclear reactor or the nuclear reactions between the accelerator charged particles and the target, only mixed radiation fields are produced, that is, beams include neutrons and photons having energies from low to high. As for BNCT of deep tumors, except the epithermal neutrons, the more the residual quantity of radiation ray is, the higher the proportion of nonselective dose deposition in the normal tissue is. Therefore, radiation causing unnecessary dose should be lowered down as much as possible. In addition, for the normal tissues of the irradiated subject, too much various radiations should be avoided, which also causes unnecessary dose deposition.

The neutron beam N generated by the neutron generating device 10 sequentially passes through the beam shaping assembly 20 and the collimator 30 and then irradiates to the irradiated subject 200 on the treatment table 40. The beam shaping assembly 20 is capable of adjusting the beam quality of the neutron beam N generated by the neutron generating device 10, and the collimator 30 is used to concentrate the neutron beam N, so that the neutron beam N has higher targeting during the treatment process. By adjusting the collimator 30, the direction of the beam and the positional relationship of the beam and the irradiated subject 200 on the treatment table 40 can be adjusted, and the position of the treatment table 40 and the irradiated subject 200 can also be adjusted to align the beam with the tumor cells M in the irradiated subject 200. These adjustments can be performed manually or automatically through a series of control mechanisms. It will be appreciated that the present disclosure may further be provided without a collimator, and the beam from the beam shaping assembly 20 directly irradiates to the irradiated subject 200 on the treatment table 40.

The beam shaping assembly 20 further includes a reflector 21, a moderator 22, a thermal neutron absorber 23, a radiation shield 24, and a beam exit 25. The neutrons generated by the neutron generating device 10 have a wide spectrum of energy, and in addition to epithermal neutrons to meet treatment needs, it is desirable to reduce other types of neutrons and photons as much as possible to avoid injury to operators or patients. Therefore, the neutrons from the neutron generating device 10 need to pass through the moderator 22 to adjust the energy (>40 keV) of fast neutrons into an epithermal neutron energy range (0.5 eV to 40 keV) and reduce thermal neutrons (<0.5 eV) as much possible. The moderator 22 is made of a material having a cross section for principally acting with fast neutrons but hardly acting with epithermal neutrons. In this embodiment, the moderator 13 is made of at least one of $D_2O$, $AlF_3$, Fluental, $CaF_2$, $Li_2CO_3$, $MgF_2$ and $Al_2O_3$. The reflector 21 surrounds the moderator 22, and reflects the neutrons diffused through the moderator 22 back to the neutron beam N to improve the utilization of the neutrons, and is made of a material having high neutron reflection ability. In this embodiment, the reflector 21 is made of at least one of Pb or Ni. A thermal neutron absorber 23, which is made of a material having a large cross section for acting with thermal neutrons, is at the rear of the moderator 22. In this embodiment, the thermal neutron absorber 23 is made of Li-6. The thermal neutron absorber 23 is used to absorb the thermal neutrons passing through the moderator 22 to reduce the content of thermal neutrons in the neutron beam N, thereby avoiding overdosing in superficial normal tissues during treatment. A radiation shield 24 around the beam exit 25 is disposed at the rear of the reflector for shielding neutrons and photons that leak from portions other than the beam exit 25. The material of the radiation shield 24 includes at least one of a photon shielding material and a neutron shielding material. In this embodiment, the material of the radiation shield 24 includes a photon shielding material lead (Pb) and a neutron shielding material polyethylene (PE). The collimator 30 is disposed at the rear of the beam exit 25, and the epithermal neutron beam emerging from the collimator 30 irradiates to the irradiated subject 200, and is slowed into thermal neutrons to reach the tumor cell M after passing through the superficial normal tissue. It will be appreciated that the beam shaping assembly 20 may have other configurations as long as the epithermal neutron beam required for treatment can be obtained.

After the irradiated subject 200 is administrated or injected boron (B-10)-containing pharmaceuticals, the boron-containing pharmaceuticals selectively accumulates in the tumor cell M, and then takes advantage that the boron (B-10)-containing pharmaceuticals have high neutron capture cross section and produces $^4$He and $^7$Li heavy charged particles through $^{10}$B(n,α)$^7$Li neutron capture and nuclear fission reaction. The two charged particles, with average energy at about 2.33 MeV, are of high linear energy transfer (LET) and short-range characteristics. LET and range of the alpha particle are 150 keV/micrometer and 8 micrometers respectively while those of the heavy charged particle $^7$Li are 175 keV/micrometer and 5 micrometers respectively, and the total range of the two particles approximately amounts to a cell size. Therefore, radiation damage to living organisms may be restricted at the cells' level. Only the tumor cells will be destroyed on the premise of having no major normal tissue damage.

In this embodiment, a radiation shielding device 50 is further disposed between the irradiated subject 200 and the beam exit 25 to shield normal tissues of the irradiated subject from irradiation by the beam from the beam exit 25. It should be understood that the radiation shielding device 50 may not be disposed.

The boron neutron capture therapy system 100 as a whole is accommodated in a building constructed by concrete. Specifically, the boron neutron capture therapy system 100 further includes an irradiation room 101 and a charged particle beam generation room 102. The irradiated subject 200 on the treatment table 40 is treated by irradiation with the neutron beam N in the irradiation room 101. The charged particle beam generation room 102 accommodates the accelerator 11. The beam shaping assembly 20 is supported by a partition wall 103 between the irradiation room 101 and the charged particle beam generation room 102. It may be understood that the partition wall 103 may completely separate the irradiation room 101 from the charged particle beam generation room 102. Alternatively, the partition wall 103 may partially separate the irradiation room 101 from charged particle beam generation room 102, and the irradiation room 101 is in communication with the charged particle beam generation room 102. There may be one or more targets T. The charged particle beam P may selectively act with one or several targets T or may simultaneously act with a plurality of targets T, to generate one or more therapeutic neutron beams N. Corresponding to the quantity of the targets T, there may also be one or more beam shaping assemblies 20, collimators 30, and treatment tables 40. A plurality of treatment tables may be disposed in the same irradiation room, or an individual irradiation room may be disposed for each treatment table.

The irradiation room 101 and the charged particle beam generation room 102 are spaces defined by a concrete wall W (including the partition wall 103). The concrete structure may shield leaking neutrons and other radiations in a working process of the boron neutron capture therapy system 100. The concrete wall W includes a reinforcing portion (described below in detail) at least partially disposed in the concrete, to increase the rigidity, tensile strength, and bearing capacity. Elastic modulus of a material of the reinforcing portion is not less than 40 GPa, yield strength of the material of the reinforcing portion is not less than 100 MPa, and ultimate strength of the material of the reinforcing portion is not less than 200 MPa. In addition, the material of the reinforcing portion is composed of elements having a cross section hardly acting with neutrons or generating radioactive isotopes with a short half-life (less than 1 year) after being activated by neutrons. Specifically, more than 90% of weight of the material of the reinforcing portion is composed of at least one element of C, H, O, N, Si, Al, Mg, Li, B, Mn, Cu, Zn, S, Ca, and Ti. In this embodiment, the material of the reinforcing portion is at least partially an aluminum alloy, a carbon fiber composite material, a glass fiber composite material or a combination thereof. When an aluminum alloy is selected, the reinforcing portion may be at least partially an aluminum-magnesium alloy. Half-life of aluminum activated by neutrons is relatively short, and is only 2.2 minutes. In a conventional reinforced concrete structure, elements such as iron, cobalt, and nickel abundantly contained in rebars have relatively long half-life after being activated by neutrons. For example, the half-life of Cobalt-60 is 5.27 years. The aluminum-magnesium alloy is selected because of the radioactivity derived from neutron activation is greatly reduced within a limited time, a secondary radiation dose is appropriately suppressed, and future device dismantlement is facilitated. The aluminum-magnesium alloy has relatively excellent mechanical properties. It should be understood that other aluminum alloys may be alternatively selected. When the carbon fiber composite material or glass fiber composite material is selected, the selected material may be a composite material of carbon fiber or glass fiber and resin. The composite material of carbon fiber or glass fiber and resin has high strength and a good anti-activation performance. It should be understood that other composite materials may be alternatively selected. The concrete structure of the partition wall 103 is described below in detail. The beam shaping assembly 20 is supported by the partition wall 103 and the reinforcing portion at least partially disposed in the partition wall 103.

FIG. 2 to FIG. 5 are a first embodiment of the partition wall 103. The partition wall 103 is a side wall. That is, the irradiation room 101 and the charged particle beam generation room 102 are horizontally disposed. An accommodating cavity 1031 is provided in the partition wall 103. The beam shaping assembly 20 is mounted in the accommodating cavity 1031. The accommodating cavity 1031 penetrates the partition wall 103 in the thickness direction. In this embodiment, the entire beam shaping assembly 20 is cylindrical, and the accommodating cavity 1031 is correspondingly a circular through hole. Because the beam shaping assembly is very sensitive to deformation and requires that the support structure have sufficient stiffness, for the partition wall 103, a reinforcing portion 1032 is disposed in the concrete structure. The reinforcing portion 1032 includes an annular rib a surrounding the beam shaping assembly 20 and frame ribs b surrounding the annular rib a. The frame ribs b includes horizontal skeletons b1 and a vertical skeletons b2. The horizontal skeletons b1 includes horizontal longitudinal ribs b11 and stirrups b12. The vertical skeletons b2 includes vertical longitudinal ribs b21 and stirrups b22. The quantity of the horizontal/vertical longitudinal ribs and the stirrups are determined according to an actual case. The reinforcing portion 1032 further includes horizontal and vertical distribution ribs c. The horizontal and vertical distribution ribs c are distributed in the entire concrete wall at a preset spacing in the horizontal direction, the vertical direction, and the thickness direction of the concrete, and the spacing is determined according to a specific case, which is schematically shown in the figures. The horizontal and vertical distribution ribs c pass through the frame ribs b, and the horizontal and vertical distribution ribs c intersecting with the annular rib a are propped on the annular rib a to improve the anchoring performance and facilitate its positioning during construction. Anchor plates d are disposed on ends of the horizontal longitudinal ribs b11 and vertical longitudinal ribs b21 to increase the bonding strength of the horizontal longitudinal ribs b11 and vertical longitudinal ribs b21. In addition to the distribution ribs propped on the annular rib, the distribution ribs may further be disposed in areas other than the frame ribs. In addition, if it is ensured that the distribution ribs and the frame ribs having a certain propping length, the anchor plate may be omitted. The materials of the annular rib a and the frame ribs b are an aluminum-magnesium alloy, a carbon fiber-resin composite material or a glass fiber-resin composite material. The material of the distribution ribs is also an aluminum-magnesium alloy, a carbon fiber-resin composite material or a glass fiber-resin composite material. Because neutrons are generated in the beam shaping assembly, the material surrounding the beam shaping assembly is most activated. It should be understood that the distribution ribs (for example, the parts other than the frame ribs) may be at least partially rebars to reduce cost, and the quantity of the distribution ribs meets the requirements of building construction to reduce the generation of radioactive nuclides. It is well known to a person skilled in the art that, during construction, the distribution ribs may further be provided with tie ribs (not shown) in the thickness direction of the concrete, and the quantity of the tie ribs is determined according to an actual case. The intersecting ribs are tied and connected by steel wires or other fixing members, such as horizontal and vertical distribution ribs, horizontal/vertical distribution ribs and tie ribs, horizontal/vertical longitudinal ribs and stirrups, and annular rib and horizontal/vertical distribution ribs. It should be understood that, for other parts of the concrete wall W which the beam shaping assembly or the like is not mounted in, only the distribution ribs may be disposed. During the construction, first, the distribution ribs of the other parts of the concrete wall, and the distribution ribs, annular ribs, and frame ribs of the partition wall 103 are tied and anchored together. Formworks at the edge of walls (including the inner wall of the accommodating cavity) is then set up to perform concrete pouring. After the pouring is completed, the beam shaping assembly is mounted in the accommodating cavity of the partition wall. It should be understood that the construction may further be performed in other manners well known to a person skilled in the art. The concrete has adequate compressive capacity and bearing capacity, the aluminum-magnesium alloy ribs and rebars have adequate tensile and bearing capacity, and the aluminum-magnesium alloy ribs and rebars configured at a tension-bearing position may compensate for insufficient tensile strength of the concrete, the stirrups are provided to improve the shear performance of the wall body, and the distribution rebars may prevent concrete from cracking and improve the overall performance of the wall body.

FIG. 6 to FIG. 9 are a second embodiment of a partition wall 103', and only the differences from the first embodiment are described below. A reinforcing portion 1032' of the partition wall 103' includes an annular section bar a' surrounding the beam shaping assembly and frame section bars b' surrounding the annular section bar a', and the frame section bars b' includes horizontal frame-section beams b1' and vertical frame-section pillars b2'. The reinforcing portion 1032' further includes horizontal and vertical distribution ribs c'. The horizontal and vertical distribution ribs c' are distributed in the entire concrete wall at a preset spacing in the horizontal direction, the vertical direction, and the thickness direction of the concrete, and the spacing is determined according to a specific case. The horizontal frame-section beams b1' and the vertical frame-section pillars b2' are connected by screw bolts, welding or other connection manners, as long as the connection strength of joints is ensured. The horizontal and vertical distribution ribs c' pass through a reserved hole of the aluminum-magnesium alloy frame section bars b' to improve the anchoring performance and ductility of the wall body. The horizontal and vertical distribution ribs c' intersecting with the annular section bar a' are propped on the annular section bar a' to improve the anchoring performance and facilitate its positioning during construction. In addition to the distribution ribs intersecting with the annular section bar, the distribution ribs may further be disposed in areas other than the frame section bars, and the distribution ribs are propped on the frame section bars. The materials of the annular section bar a' and frame section bars b' are an aluminum-magnesium alloy, a carbon fiber-resin composite material or a glass fiber-resin composite material. The material of the distribution ribs is also an aluminum-magnesium alloy, a carbon fiber-resin composite material or a glass fiber-resin composite material. Because neutrons are generated in the beam shaping assembly, the material surrounding the beam shaping assembly is most activated. It should be understood that the distribution ribs (for example, the parts other than the frame section bars) may be at least partially rebars to reduce cost, and the quantity of the distribution ribs meets the requirements of building construction to reduce the generation of radioactive nuclides. It is well known to a person skilled in the art that, during the art that, the art that, during construction, the distribution ribs may further be provided with tie ribs (not shown) in the thickness direction of the concrete, and the quantity of the tie ribs is determined according to an actual case. The intersecting ribs are tied and connected by steel wires or other fixing members such as horizontal and vertical distribution ribs, horizontal/vertical distribution ribs and tie ribs and annular section bar and horizontal/vertical distribution ribs. In this embodiment, the cross-section of the aluminum-magnesium alloy section bars is H-shaped. It should be understood that the cross-section may have another shape. During the construction, first, the distribution ribs of the other parts of the concrete wall and the distribution ribs, annular section bar, and frame section bars of the partition wall 103' are tied and anchored together. Formworks at the edge of walls (including the inner wall of the accommodating cavity) is then set up to perform concrete pouring. After the pouring is completed, the beam shaping assembly is mounted in the accommodating cavity of the partition wall. It should be understood that the construction may further be performed in other manners well known to a person skilled in the art. The concrete has high compressive strength but low tensile strength, and the strain slowly increases with time under a constant stress. The aluminum-magnesium alloy section bars has adequate tensile strength and shear strength and high stiffness, and the strain does not increase with time under a constant stress, and can compensate for insufficient mechanical properties and material characteristics of the concrete. The distribution rebars may prevent concrete from cracking and improve the overall performance of the wall body.

It should be understood that the reinforcing portion of the partition wall may further be a combination of the foregoing two embodiments. For example, the reinforcing portion may include the annular rib surrounding the beam shaping assembly and the frame section bars surrounding the annular rib, or may include the annular section bar surrounding the beam shaping assembly and the frame ribs surrounding the annular section bar.

Figure 10:
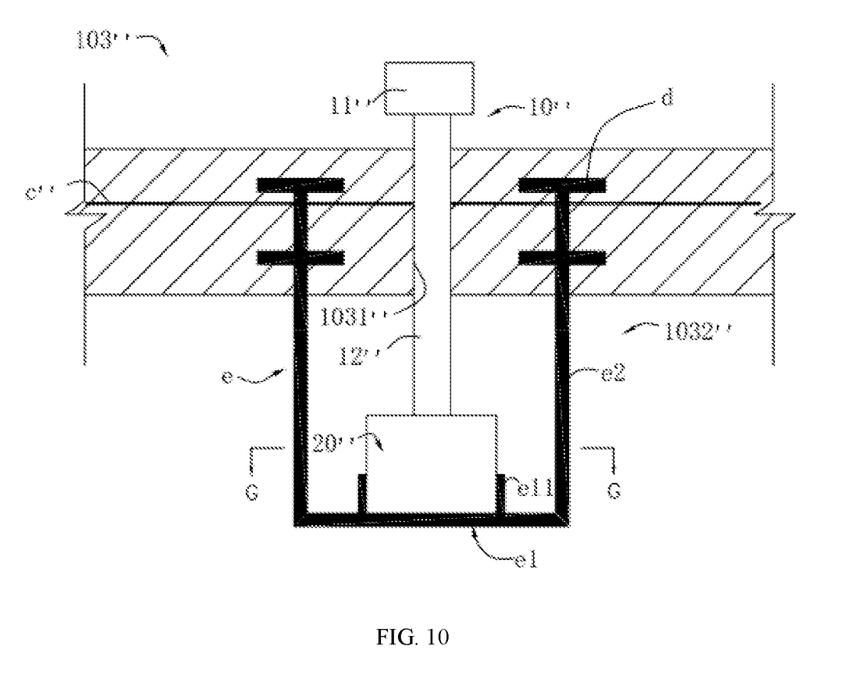
FIG. 10 is a schematic diagram of a support structure of a beam shaping assembly of a neutron capture therapy system according to a third embodiment of the present disclosure.
Figure 11:
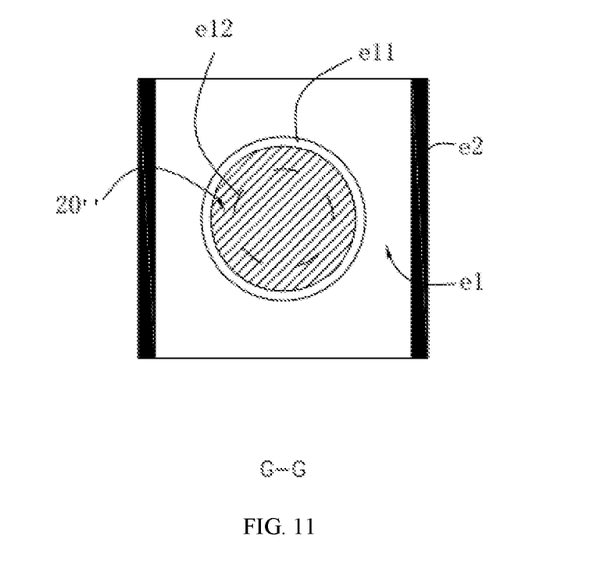
FIG. 11 is a schematic sectional view along G-G in FIG. 10.

FIG. 10 and FIG. 11 are a third embodiment of a partition wall 103". In this embodiment, the irradiation room and the charged particle beam generation room are vertically disposed. That is, the partition wall 103" is a floor slab (a floor or a ceiling). A neutron generating device 10" further includes a beam transmitter 12", the beam transmitter 12" transmits the charged particle beam generated by an accelerator 11" to the target, a through hole 1031" is provided in the partition wall 103", and the beam transmitter 12" passes through the through hole 1031". A reinforcing portion 1032" of the partition wall 103" includes a first reinforcing portion d and a second reinforcing portion e, the first reinforcing portion d is disposed in the concrete of the partition wall 103", the second reinforcing portion e at least partially extends from the concrete of the partition wall 103", the second reinforcing portion e includes a horizontal support plate e1 and side plates e2 connecting the support plate e1 to the first reinforcing portion d, and a beam shaping assembly 20" is supported on the horizontal support plate e1. In this embodiment, the second reinforcing portion e is a square-U-shaped groove structure, there are two opposite side plates e2, and the material is an aluminum-magnesium alloy, a carbon fiber-resin composite material or a glass fiber-resin composite material to reduce the generation of radioactive nuclides. Considering that the structural steel has high strength, adequate plasticity and toughness, uniform material and adequate weldability, a steel material may be used. It should be understood that other materials or other forms of construction may be used. A flange e11 is disposed on a side, facing the first reinforcing portion d, of the support plate e1, the beam shaping assembly 20" is located in the flange e11, and the flange e11 limits the beam shaping assembly 20" in the horizontal direction. In this embodiment, the entire beam shaping assembly is cylindrical, and the corresponding flange is an annular reinforcing rib. A through hole e12 is also formed in the support plate e1, and the neutron beam N generated by the neutron generating device 10" emerges from the through hole e12 after passing through the beam shaping assembly 20". In this embodiment, the through hole e12 is formed by cutting on the support plate e1.

The first reinforcing portion increases the strength of the edge of the floor slab hole (the through hole) in one aspect, and provides support to the beam shaping assembly in another aspect. The first reinforcing portion may include the frame ribs/section bars and the annular rib/section bar according to the reinforcing portion construction of the foregoing embodiments. Because a floor slab is used herein, the frame ribs or frame section bars only includes the horizontal skeletons or horizontal frame-section beams, and the vertical skeletons or vertical frame-section pillars are replaced with the horizontal skeletons or horizontal frame-section beams. The specific construction is not described in detail herein, and only two section beams are shown in the figures. When the first reinforcing portion is constructed by the frame section bars, the side plates e2 and the frame section bars are connected by welding or screw bolts. It should be understood that other connection manners may be used, as long as the connection strength is ensured. When the first reinforcing portion is constructed by the frame ribs, anchor plates are disposed at an end of the side plates e2, which is anchored to the frame ribs. Considering the forces applied to the floor slab and the first reinforcing portion in the vertical direction, the horizontal skeletons or horizontal frame-section beams connected to the side plates extend over the entire length of the floor slab. The reinforcing portion 1032" same as the foregoing embodiments further includes (horizontal) distribution ribs c", tie ribs (not shown), and the like. The distribution ribs c" are distributed in the concrete at a preset spacing in the horizontal direction and the thickness direction of the concrete. During the construction, first, the distribution ribs of the other parts of the concrete wall and the distribution ribs, frame ribs/section bars, and annular rib/section bar of the partition wall 103" are tied and anchored together. The second reinforcing portion is welded or anchored to the first reinforcing portion. Formworks at the edge of walls (including the inner wall of the through hole) is then set up to perform concrete pouring. After the pouring is completed, the beam shaping assembly is mounted in the flange from a side of the second reinforcing portion without a side plate, and the beam transmitter is mounted passing through the through hole. It should be understood that the construction may further be performed in other manners well known to a person skilled in the art.

The boron neutron capture therapy system 100 may further include a preparation room, a control room, and another space used to assist in treatment. Each irradiation room may be provided with one preparation room used for preparation work, for example, securing an irradiated subject to a treatment table, injecting boron-containing pharmaceuticals, and simulating a treatment plan before treatment with irradiation. A connecting passage may be disposed between the preparation room and the irradiation room, and after the preparation work is completed, the irradiated subject may be directly pushed into the irradiation room or a control mechanism may control automatic entry of the irradiated subject into the irradiation room by a rail. The control room is configured to control the accelerator, the beam transmitting device, the treatment table, and the like, and control and manage the entire irradiation process. A manager may further simultaneously monitor a plurality of the irradiation rooms in the control room.

In this embodiment, the concrete wall is a boron-containing barite concrete wall with the thickness of greater than 1 m and the density of 3 g/c.c. The boron-containing concrete has better neutron absorption property, so that the radiation shielding effect of the concrete is enhanced, and metal materials in the concrete may also be exposed to a smaller amount of neutrons. It should be understood that the concrete wall may have another thickness or density or may be made of another material, and different parts of the concrete wall may have different thicknesses, densities or materials. It should be understood that the present invention may further be applied to other types of neutron irradiation systems.

Although the illustrative embodiments of the present invention have been described above in order to enable those skilled in the art to understand the present invention, it should be understood that the present invention is not to be limited the scope of the embodiments. For those skilled in the art, as long as various changes are within the spirit and scope as defined in the present invention and the appended claims, these changes are obvious and within the scope of protection claimed by the present invention.

What is claimed is:

1. A neutron capture therapy system comprising:
   a neutron generating device comprising an accelerator and a target, wherein a charged particle beam generated by acceleration of the accelerator acts with the target to generate a neutron beam;

a beam shaping assembly comprising:
  a moderator configured to moderate the neutrons generated from the target to an epithermal neutron energy range,
  a reflector surrounding the moderator, wherein the reflector directs deviating neutrons back to the moderator to enhance intensity of an epithermal neutron beam,
  a thermal neutron absorber provided to absorb thermal neutrons to avoid overdosing in superficial normal tissues during treatment,
  a radiation shield provided to shield leaking neutrons and photons so as to reduce dose to normal tissues in a non-irradiation area, and
  a beam exit, wherein the radiation shield around the beam exit is disposed at the rear of the reflector;
  a concrete wall accommodating the neutron generating device and the beam shaping assembly; and
  a reinforcing portion at least partially disposed in the concrete wall;
  wherein the concrete wall and the reinforcing portion are provided to support the beam shaping assembly, and more than 90% of weight of a material of the reinforcing portion is composed of at least one element of C, H, O, N, Si, Al, Mg, Li, B, Mn, Cu, Zn, S, Ca, and Ti.

2. The neutron capture therapy system according to claim 1, wherein elastic modulus of the material of the reinforcing portion is not less than 40 GPa, yield strength of the material is not less than 100 MPa, ultimate strength of the material is not less than 200 MPa.

3. The neutron capture therapy system according to claim 1, wherein half-life of radioactive isotopes generated after the reinforcing portion is activated by neutrons is less than 1 year.

4. The neutron capture therapy system according to claim 1, wherein the material of the reinforcing portion is at least partially an aluminum alloy, a carbon fiber composite material or a glass fiber composite material.

5. The neutron capture therapy system according to claim 1, wherein the neutron capture therapy system further comprises a treatment table and a collimator, the collimator is disposed at the rear of the beam exit to converge the neutron beam, the neutron beam generated by the neutron generating device passes through the beam shaping assembly and the collimator to irradiate an irradiated subject on the treatment table, and a radiation shielding device is disposed between the irradiated subject and the beam exit to shield normal tissues of the irradiated subject from irradiation by beams from the beam exit.

6. The neutron capture therapy system according to claim 5, wherein the neutron capture therapy system further comprises a charged particle beam generation room and an irradiation room, the irradiated subject on the treatment table receives treatment of neutron beam irradiation in the irradiation room, the charged particle beam generation room accommodates the accelerator, and the concrete wall comprises a partition wall between the charged particle beam generation room and the irradiation room.

7. The neutron capture therapy system according to claim 6, wherein the beam shaping assembly is disposed in the partition wall and supported by the partition wall, an accommodating cavity is provided in the partition wall, the beam shaping assembly is mounted in the accommodating cavity, and the accommodating cavity penetrates the partition wall in the thickness direction.

8. The neutron capture therapy system according to claim 6, wherein the neutron generating device further comprises a beam transmitter, the beam transmitter transmits the charged particle beam generated by the accelerator to the target, a through hole is provided in the partition wall, the beam transmitter passes through the through hole, the reinforcing portion is at least partially disposed in the partition wall, and the beam shaping assembly is supported on the reinforcing portion.

9. A neutron capture therapy system comprising:
  a neutron generating device configured to generate a neutron beam;
  a beam shaping assembly configured to adjust beam quality of the neutron beam;
  a support device for holding the beam shaping assembly, wherein the support device comprises an accommodating cavity, the beam shaping assembly is mounted in the accommodating cavity, and the support device further comprises a concrete wall and a reinforcing portion at least partially disposed in the concrete wall.

10. The neutron capture therapy system according to claim 9, wherein elastic modulus of a material of the reinforcing portion is not less than 40 GPa, yield strength of the material is not less than 100 MPa, ultimate strength of the material is not less than 200 MPa.

11. The neutron capture therapy system according to claim 9, wherein more than 90% of weight of a material of the reinforcing portion is composed of at least one element of C, H, O, N, Si, Al, Mg, Li, B, Mn, Cu, Zn, S, Ca, and Ti, and half-life of radioactive isotopes generated after the reinforcing portion is activated by neutrons is less than 1 year.

12. The neutron capture therapy system according to claim 9, wherein the accommodating cavity is a through hole formed in the concrete wall, the reinforcing portion comprises a circular ring disposed around the beam shaping assembly, a frame disposed around the circular ring, and distribution ribs distributed in the concrete at a preset spacing in the horizontal direction, the vertical direction, and the thickness direction of the concrete; the distribution ribs at least partially pass through the frame or are at least partially propped on the frame, the distribution ribs are at least partially propped on the circular ring.

13. The neutron capture therapy system according to claim 12, wherein materials of the circular ring and the frame are an aluminum alloy, a carbon fiber composite material or a glass fiber composite material, and a material of the distribution ribs is steel, an aluminum alloy, a carbon fiber composite material or a glass fiber composite material.

14. The neutron capture therapy system according to claim 13, wherein the aluminum alloy is an aluminum-magnesium alloy, the carbon fiber composite material is a carbon fiber-resin composite material, and the glass fiber composite material is a glass fiber-resin composite material.

15. The neutron capture therapy system according to claim 12, wherein the circular ring is a section bar or constructed by a rib, the frame is section bars or constructed by ribs; when the frame is section bars, the frame comprises horizontal frame-section beams and vertical frame-section pillars, and the horizontal frame-section beams and the vertical frame-section pillars are connected by screw bolts or welding; when the frame is constructed by ribs, the frame comprises horizontal skeletons and vertical skeletons, the horizontal skeletons comprise horizontal longitudinal ribs and stirrups, and the vertical skeletons comprise vertical longitudinal ribs and stirrups.

16. The neutron capture therapy system according to claim 9, wherein the reinforcing portion comprises a first reinforcing portion and a second reinforcing portion, the first reinforcing portion is disposed in the concrete wall, and the second reinforcing portion at least partially extends from the concrete wall.

17. The neutron capture therapy system according to claim 16, wherein the first reinforcing portion comprises a circular ring, a frame, and distribution ribs, the circular ring is a section bar or constructed by a rib, the frame is constructed by horizontal frame-section beams or horizontal skeletons, and the horizontal skeletons comprise horizontal longitudinal ribs and stirrups.

18. The neutron capture therapy system according to claim 16, wherein the second reinforcing portion comprises a horizontal support plate and side plates connecting the support plate to the first reinforcing portion; a flange is disposed on a side, facing the first reinforcing portion, of the support plate, the flange forms the accommodating cavity and limits the beam shaping assembly in the horizontal direction; a through hole is formed in the support plate, and the neutron beam emerges from the through hole after passing through the beam shaping assembly.

19. The neutron capture therapy system according to claim 16, wherein a material of the second reinforcing portion is an aluminum alloy, a carbon fiber composite material, or a glass fiber composite material.

* * * * *